(12) United States Patent
Mulero et al.

(10) Patent No.: US 9,029,088 B2
(45) Date of Patent: May 12, 2015

(54) HUMAN SINGLE NUCLEOTIDE POLYMORPHISMS WITHIN CODIS LOCI D13S317, TH01, VWA, D12S391, AND D6S1043

(75) Inventors: Julio Mulero, Sunnyvale, CA (US); Michael Malicdem, Santa Clara, CA (US); Robert Lagace, Oakland, CA (US)

(73) Assignee: Life Technologies Corporation, Carlsbad, CA (US)

( * ) Notice: Subject to any disclaimer, the term of this patent is extended or adjusted under 35 U.S.C. 154(b) by 1154 days.

(21) Appl. No.: 12/905,916

(22) Filed: Oct. 15, 2010

(65) Prior Publication Data
US 2011/0183857 A1    Jul. 28, 2011

Related U.S. Application Data

(60) Provisional application No. 61/252,141, filed on Oct. 15, 2009.

(51) Int. Cl.
*C12Q 1/68*    (2006.01)
*C07H 21/00*   (2006.01)

(52) U.S. Cl.
CPC ............ *C12Q 1/6858* (2013.01); *C12Q 1/6888* (2013.01); *C12Q 2525/117* (2013.01); *C12Q 2563/107* (2013.01)

(58) Field of Classification Search
None
See application file for complete search history.

(56) References Cited

U.S. PATENT DOCUMENTS

| 7,008,771 B1 | 3/2006 | Schumm et al. |
| 2009/0142764 A1 | 6/2009 | Hennessy et al. |

FOREIGN PATENT DOCUMENTS

WO    03/020739    3/2003

OTHER PUBLICATIONS

Applied Biosystems, "AmpFISTR Identifier PCR Amplification Kit User's Manual", *Applied Biosystems*, 2001, pp. i-x and 1-1 to 1-10.
Babu, et al., "Aryl-β-C-LNA Monomers as Universal Hybridization Probes[1],[2]", *Nucleosides, Nucleotides & Nucleic Acids Journal*, vol. 22, Issue 5,, 2003, pp. 1317-1319.
Berger, et al., "Stable and Selective Hybridization of Oligonucleotides with Unnatural Hydrophobic Bases", *Angew. Chem. Int. Ed. Engl.*, vol. 39, No. 16, 2000, pp. 2940-2942.
Berger, et al., "Universal bases for hybridization, replication and chain termination", *Nucleic Acids Research*, vol. 28, Issue 15,, Aug. 1, 2000, pp. 2911-2914.
Bergstrom, et al., "Comparison of the base pairing properties of a series of nitroazole nucleobase analogs in the oligodeoxyribonucleotide sequence 5'- d(CGCXAATTYGCG)-3"", *Nucleic Acids Research*, vol. 25, Issue 10,, May 1997, pp. 1935-1942.
Bergstrom, et al., "Synthesis, structure and biochemical applications of a universal nucleic-acid spacer-1-(2'-deoxy-β-d-ribofuranosyl)-3-nitropyrrole", *Abstract of Papers of the American Chemical Society*, vol. 206, No. 2, 1993, p. 308-ORGN.

(Continued)

*Primary Examiner* — Samuel Woolwine
*Assistant Examiner* — Danna Bicknell

(57) ABSTRACT

Disclosed are methods for human identification utilizing newly discovered single nucleotide polymorphisms (SNPs) within CODIS loci D13S317, TH01, vWA, D12S391 and D6S1043, which can cause allelic dropout. Also disclosed are kits useful in human identification.

4 Claims, 1 Drawing Sheet

D13S317:  5' CTTTAGTGGGCATCCGTGACTCTCTGGACTCTGACCCATCTAA(C/T)GCCTAT 3'    SEQ ID NO:1

TH01:     5' CCTGTACACAGGGCTTCCGAGTGCAGGTCACAGGGAACACAGACT(C/A)CATGGT 3'   SEQ ID NO:2 vWA:      5' TC(C/T)ATC(T/C)ATCCATC(C/T)ATCCTATGTATTTATCATCTGTCCTATCTCT 3'   SEQ ID NO:3

D12S391:  5' GCACTCCAGGTTCTCAGGCCTTCCACCTGGGATGGATAATTACACCAT(C/T)AGT 3'   SEQ ID NO:4

D6S1043:  5' TGACTTGGACTGAGATTTACACAATTGGCTTC(C/T)CTTGTTCTGAGGCTTTTGTA 3'   SEQ ID NO:5

(Predominant/Variant SNP)

(56) References Cited

OTHER PUBLICATIONS

Bergstrom, D. et al., "Synthesis, Structure, and Deoxyribonucleic Acid Sequencing with a Universal Nucleoside: I-(2'-Deoxy-β-D-ribofuranosyl)-3-nitropyrrole", *J. Am. Chem. Soc.*, vol. 117(4), 1995, pp. 1201-1209.

Butler, et al., "Forensic DNA Typing", *Second Edition: Biology, Technology, and Genetics of STR Markers*, Mar. 8, 2005, pp. 85-121.

Girgis, et al., "Synthesis of 2'-deoxyribofuranosyl indole nucleosides related to the antibiotics SF-2140 and neosidomycin", *Journal of Heterocyclic Chemistry*, vol. 25, Issue 2, Mar./Apr. 1988, pp. 361-366.

Guckian, et al., "Experimental Measurement of Aromatic Stacking Affinities in the Context of Duplex DNA", *Journal of the American Chemical Society*, vol. 118, Issue 34, Aug. 28, 1996, pp. 8182-8183.

Guckian, et al., "Factors Contributing to Aromatic Stacking in Water: Evaluation in the Context of DNA", *Journal of the American Chemical Society*, vol. 122, Issue 10, Mar. 15, 2000, pp. 2213-2222.

Loakes, et al., "5-Nitroindole as an universal base analogue", *Nucleic Acids Research*, vol. 22, Issue 20, Oct. 11, 1994, pp. 4039-4043.

Loakes, et al., "5'-Tailed Octanucleotide Primers for Cycle Sequencing", *Nucleosides, Nucleotides & Nucleic Acids Journal*, vol. 18, Issue 11 & 12, Nov. 1999, pp. 2685-2695.

Loakes, et al., "Enzymatic Recognition Acryclic Universal Base Analogues in Oligonucleotides", *Nucleosides, Nucleotides & Nucleic Acids Journal*, vol. 15, Issue 11 & 12, Nov. 1996, pp. 1891-1904.

Loakes, "Survey and Summary: The applications of universal DNA base analogues", *Nucleic Acids Research*, vol. 29, Issue 12, Jun. 2001, pp. 2437-2447.

Matulic-Adamic, et al., "Synthesis and Structure of 1-Deoxy-1-phenyl-β-d-ribofuranose and Its Incorporation into Oligonucleotides", *The Journal of Organic Chemistry*, vol. 61, Issue 11, May 31, 1996, pp. 3909-3911.

Millican, et al., "Synthesis and biophysical studies of short oligodeoxinucleotides with novel modifications: a possible approach to the problem of mixed base oligodeoxynucleotide synthesis", *Nucleic Acids Research*, vol. 12, Issue 19, Oct. 11, 1984, pp. 7435-7453.

Nichols, et al., "A universal nucleoside for use at ambiguous sites in DNA primers", *Nature*, vol. 369, No. 6480, Jun. 9, 1994, pp. 492-493.

Papageorgious, et al., "Nucleosides and nucleotides. Part 25.†. Synthesis of a protected 1-(2'-deoxy-β-D-ribofuranosyl)-1 H-benzimidazole 3'-phosphate", *Helvetica Chimica Acta*, vol. 70, Issue 1, Feb. 4, 1987, pp. 138-141.

PCTUS1052935, "International Search Report and Written Opinion Received mailed on Feb. 10, 2011", 6 pages.

Rozen, S. et al., "Primer3 on the WWW for General Users and for Biologist Programmers", *Methods in Molecular Biology*, vol. 132: Bioinformatics Methods and Protocols, 2000, pp. 365-386.

Seela, et al., "Oligodeoxyribonucleotides Containing 4-Aminobenzimidazole in Place of Adenine: Solid-phase synthesis and base pairing", *Helvetica Chimica Acta*, vol. 78, Issue 4, Jun. 1995, pp. 833-846.

Seela, et al., "Synthesis of 4-Substituted 1H-Benzimidazole 2'-Deoxyribonucleosides and Utility of the 4-Nitro Compound as Universal Base", *Helvetica Chimica Acta*, vol. 79, Issue 2, Mar. 20, 1996, pp. 488-498.

Seela, et al., "The N8-(2'deoxyribofuranoside) of 8-aza-7-deazaadenine: a universal nucleoside forming specific hydrogen bonds with the four canonical DNA constituents", *Nucleic Acids Research*, vol. 28(17), 2000, pp. 3224-3232.

Smith, et al., "Use of 5-Nitroindole-2'deoxyribose-5'-triphosphate for Labelling and Detection of Oligonucleotides 1", *Nucleosides, Nucleotides & Nucleic Acids Journal*, vol. 17, Issue 1-3, Jan. 1998, pp. 555-564.

Van Aerschot, et al., "An acyclic 5-nitroindazole nucleoside analogue as ambiguous nucleoside", *Nucleic Acids Research*, vol. 23, Issue 21,, 1995, pp. 4363-4370.

Van Aerschot, et al., "In Search of Acyclic Analogues as Universal Nucleosides in Degenerate Probes", *Nucleosides, Nucleotides & Nucleic Acids*, vol. 14, Issue 3-5, May 1995, pp. 1053-1056.

Wu, et al., "Efforts toward Expansion of the Genetic Alphabet: Optimization of Interbase Hydrophobic Interactions", *Journal of the American Chemical Society*, vol. 122, Issue 32, Aug. 16, 2000, pp. 7621-7632.

| | |
|---|---|
| D13S317: 5' CTTTAGTGGGCATCCGTGACTCTCTGGACTCTGACCCATCTAA(C/T)GCCTAT 3' | SEQ ID NO:1 |
| TH01: 5' CCTGTACACAGGGCTTCCGAGTGCAGGTCACAGGGAACACAGACT(C/A)CATGGT 3' | SEQ ID NO:2 |
| vWA: 5' TC(C/T)ATC(T/C)ATC(C/T)ATCCTATGTATTTATCATCTGTCCTATCTCT 3' | SEQ ID NO:3 |
| D12S391: 5' GCACTCCAGGTTCTCAGGCCTTCCACCTGGGATGGATAATTACACACCAT(C/T)AGT 3' | SEQ ID NO:4 |
| D6S1043: 5' TGACTTGGACTGAGATTTACACAATTGGCTTC(C/T)CTTGTTCTGAGGCTTTTGTA 3' | SEQ ID NO:5 |

(Predominant/Variant SNP)

HUMAN SINGLE NUCLEOTIDE POLYMORPHISMS WITHIN CODIS LOCI D13S317, TH01, VWA, D12S391, AND D6S1043

This application claims priority to U.S. Provisional Application No. 61/252,141, filed Oct. 15, 2009 which is incorporated by reference herein in its entirety for any purpose.

FIELD

In general, the disclosed invention relates to the identification of new single nucleotide polymorphisms (SNPs) within STR loci on human chromosomes.

BACKGROUND

The fields of forensics, paternity testing, tissue typing, and personalized medicine routinely use DNA-based techniques for identity determinations, genotyping, phenotypic prediction, and in the prediction and/or prevention of disease. DNA typing involves the analysis of alleles of genomic DNA with characteristics of interest, commonly referred to as "markers." Most typing methods in use today are specifically designed to detect and analyze differences in the length and/or sequence of one or more regions of DNA markers known to appear in at least two different forms in a population. Such length and/or sequence variation is referred to as "polymorphism." Any region (i.e., "locus") of DNA in which such a variation occurs is referred to as a "polymorphic locus."

In recent years, the discovery and development of polymorphic short tandem repeats (STRs) as genetic markers has played an important role in DNA typing. STRs have become the primary means for human identity and forensic DNA testing. The Combined DNA Index System (CODIS) DNA database operated by the Federal Bureau of Investigation stores the DNA profile information of selected individuals. The profile includes 13 STR markers (13 loci with STR repeats), two additional allelic markers and AMEL, a sex determination allele. The selected DNA profiles are from convicted offenders, forensic, arrestee, missing or unidentified persons, and missing persons reference DNA (blood relative). Comparison of the DNA profile of an unidentified sample to CODIS DNA profiles has provided potential identification matches or investigative leads of possible perpetrators.

Matching DNA profiles produced from existing commercial STR assays with improved STR assays provides continuity and comparability of the DNA profiles within and between databases. An alteration in the DNA sequence due to, for example, a heretofore unknown mutation, polymorphism or re-arrangement, can result in allelic dropout (the failure or significantly reduced amplification of a target nucleic acid). The occurrence of allelic dropout in new STR assays can make DNA profile matching within and between databases difficult or imprecise. Thus, careful design of new assays such that all potential amplification products are detected in as large a portion of the population as possible remains an ongoing concern when developing new STR assays. Therefore, there exists a need in the art, to improve DNA-based technologies based on the discovery of new variations in human DNA sequences.

SUMMARY OF SOME EMBODIMENTS OF THE INVENTION

In some embodiments, disclosed is a method for human identification. In some embodiments, methods for human identification comprise: hybridizing a first primer to a locus comprising a first primer binding site in a target nucleic acid sequence from a human nucleic acid sample to be analyzed; hybridizing a second primer to a second primer binding site in said locus wherein said second primer hybridizes to a single nucleotide polymorphism (SNP) nucleobase in said second primer binding site, wherein the locus is selected from D13S317, TH01, vWA, D12S391, and D6S1043; and amplifying the target nucleic acid sequence, wherein the amplifying yields at least a first amplified sequence comprising at least one SNP as described in SEQ ID NO:1, SEQ ID NO:2, SEQ ID NO:3, SEQ ID NO:4 and SEQ ID NO:5 and Table 1.

In some embodiments, the amplified sequence is amplified by PCR and the amplified sequence is detected by sequencing of the amplified sequence. In some embodiments, sequencing identifies at least one predominant or variant SNP in the target nucleic acid sequence.

In some embodiments each of the five loci supra are amplified by PCR, sequenced and SNPs are identified. In some embodiments, each locus has short tandem repeats (STRs) which characterize alleles of a locus in a human. In some embodiments the determination of the alleles for a plurality of loci identifies a human.

In some embodiments, the 3' terminus of the second primer comprises the predominant SNP and a third primer comprises the variant SNP at the 3' terminus. In other embodiments, the second primer comprises a universal base that is complementary to the SNP in the second primer binding site, wherein the universal base is the 3' terminus nucleobase of the second primer, wherein the universal base is selected from the group consisting of Inosine, Xanthosine, 3-nitropyrrole, 4-nitroindole, 5-nitroindole, 6-nitroindole, nitroimidazole, 4-nitropyrazole, 5-aminoindole, 4-nitrobenzimidazole, 4-aminobenzimidazole, phenyl C-ribonucleoside, benzimidazole, 5-fluoroindole, indole; acyclic sugar analogs, derivatives of hypoxanthine, imidazole 4,5-dicarboxamide, 3-nitroimidazole, 5-nitroindazole; aromatic analogs, benzene, naphthalene, phenanthrene, pyrene, pyrrole, difluorotoluene; isocarbostyril nucleoside derivatives, MICS, ICS; and hydrogen-bonding analogs, N8-pyrrolopyridine.

In some embodiments, at least one of the first or second primer comprises a label, wherein said label is fluorescent and the fluorescent label is selected from 5-carboxyfluorescein (FAM™ dye), and 2'7'-dimethoxy-4'5'-dichloro-6-carboxy-fluorescein (JOE™ dye), fluorescein (FL); N,N,N',N'-tetramethyl-6-carboxyrhodamine (TAMRA™ dye); 6-carboxy-X-rhodamine (ROX™ dye); CY3™ dye; CY5™ dye; tetrachloro-fluorescein (TET™ dye); and hexachloro-fluorescein (HEX™ dye); NED™ dye; 6-FAM™ dye; VIC® dye; PET® dye; LIZ®dye, SID™ dye, TED™ dye, and TAZ™ dye.

In some embodiments, disclosed is a method of human identification. In some embodiments, methods for human identification comprise: amplifying at least one locus, comprising at least one SNP from Table 1, said locus selected from D13S317, TH01, vWA, D12S391, and D6S1043, for at least one nucleic acid sample to be analyzed, wherein the amplifying yields at least one amplified allele within an amplification product; detecting the at least one amplified allele, wherein the at least one amplified allele contains the at least one SNP, wherein the at least one allele is indicative of the identity of a human, wherein the amplifying step comprises-hybridizing a sequence specific oligonucleotide to the nucleic acid sequence close to the at least one locus so as to permit generation of the amplification product comprising the SNP(s) from the at least one locus, wherein the sequence specific oligonucleotide hybridizes to the SNP nucleobase in the at least one amplified allele. The method further comprises: identifying the SNP(s) in the amplified allele(s), wherein identifying comprises sequencing the amplification product(s), wherein the SNP(s) of each allele(s) is identified. In some embodiments, the amplifying comprises at least two loci, a multiplex amplification reaction, and separating the amplified alleles prior to the detecting step, wherein separating is by capillary gel electrophoresis. In some embodiments, amplifying comprises a plurality of loci being amplified, using a pair of oligonucleotide primers for each locus, wherein at least one primer of each pair of oligonucleotide primers is a labeled primer, wherein the labeled primer comprises a fluorescent label.

In some embodiments, each primer pair for each locus of the plurality of loci, being amplified by PCR comprises a different fluorescent label covalently attached thereto, wherein when four labeled primers comprises four different fluorescent labels for four separate loci and wherein the amplifying comprises a different fifth fluorescent label, wherein the fifth label is attached to a size standard, wherein the different fluorescent labels comprise a first fluorescent label which emits its maximum fluorescence at 520 nm, a second fluorescent label which emits its maximum fluorescence at 550 nm, a third fluorescent label which emits its maximum fluorescence at 575 nm, a fourth fluorescent label which emits its maximum fluorescence at 590 nm, a fifth fluorescent label which emits its maximum fluorescence at 650 nm, or a fluorescent label which emits its maximum fluorescence at 620 nm.

In some embodiments, the sample used for human identification may be from one or more of hair, feces, blood, tissue, urine, saliva, cheek cells, vaginal cells, skin, for example skin cells contained in fingerprints, bone, tooth, buccal sample, amniotic fluid containing placental cells, and amniotic fluid containing fetal cells and semen.

In some embodiments, the method for human identification further comprises comparing the allele(s) in the at least one locus selected from D13S317, TH01, vWA, D12S391, and D6S1043 identified in a known human nucleic acid sample with the allele(s) found in the at least one locus amplified in the unidentified human nucleic acid sample, wherein the known human nucleic acid sample is analyzed in parallel to the unidentified human nucleic acid sample.

In some embodiments, disclosed is a nucleic acid comprising at least one SNP nucleobase within a sequence selected from SEQ ID NO: 1, SEQ ID NO:2, SEQ ID NO:3, SEQ ID NO:4 and SEQ ID NO:5, wherein at least one SNP nucleobase is within a locus selected from D13S317, TH01, vWA, D12S391, and D6S1043, and wherein at least two and at least three SNP nucleobases are within SEQ ID NO:3. In some embodiments, the SNP nucleobase is within a primer binding site, wherein the 3' terminus of a primer binds to the SNP nucleobase within the primer binding site, wherein the 3' terminus of the primer comprises either the predominant or variant SNP nucleobase or a universal base.

In some embodiments, the method of human identification comprises determining the allele of a genetic marker D13S317 on a first chromosome, wherein the marker comprises a SNP from Table 1; and determining the allele of genetic marker D13S317 on a second chromosome, wherein the marker does not comprise a SNP from Table 1, wherein the allele of the genetic marker is amplified by an oligonucleotide primer pair, wherein one primer of the primer pair comprises a nucleobase or a universal base complementary to the SNP of SEQ ID NO:1, by a polymerase chain reaction (PCR) and the allele is identified by capillary electrophoresis. In some embodiments, neither primer of the primer pair comprises a nucleobase complementary to the SNP. In some embodiments, the genetic marker of the first chromosome and the genetic marker of the second chromosome are amplified by PCR.

In some embodiments, the method of human identification comprises determining the allele of a genetic marker TH01 on a first chromosome, wherein the marker comprises a SNP from Table 1; and determining the allele of genetic marker TH01 on a second chromosome, wherein the marker does not comprise a SNP from Table 1, wherein the allele of the genetic marker is amplified by an oligonucleotide primer pair, wherein one primer of the primer pair comprises a nucleobase or a universal base complementary to the SNP of SEQ ID NO:2, by a polymerase chain reaction (PCR) and the allele is identified by capillary electrophoresis. In some embodiments, neither primer of the primer pair comprises a nucleobase complementary to the SNP. In some embodiments, the genetic marker of the first chromosome and the genetic marker of the second chromosome are amplified by PCR.

In some embodiments, the method of human identification comprises determining the allele of a genetic marker vWA on a first chromosome, wherein the marker comprises at least one SNP from Table 1; and determining the allele of genetic marker vWA on a second chromosome, wherein the marker does not comprise at least one SNP from Table 1, wherein the allele of the genetic marker is amplified by an oligonucleotide primer pair, wherein one primer of the primer pair comprises a nucleobase or a universal base complementary to at least one SNP of SEQ ID NO:3, by a polymerase chain reaction (PCR) and the allele is identified by capillary electrophoresis. In some embodiments, neither primer of the primer pair comprises a nucleobase complementary to at least one SNP. In some embodiments, the genetic marker of the first chromosome and the genetic marker of the second chromosome are amplified by PCR.

In some embodiments, the method of human identification comprises determining the allele of a genetic marker D12S391 on a first chromosome, wherein the marker comprises a SNP from Table 1; and determining the allele of genetic marker D12S391 on a second chromosome, wherein the marker does not comprise a SNP from Table 1, wherein the allele of the genetic marker is amplified by an oligonucleotide primer pair, wherein one primer of the primer pair comprises a nucleobase or a universal base complementary to the SNP of SEQ ID NO:4, by a polymerase chain reaction (PCR) and the allele is identified by capillary electrophoresis. In some embodiments, neither primer of the primer pair comprises a nucleobase complementary to the SNP. In some embodiments, the genetic marker of the first chromosome and the genetic marker of the second chromosome are amplified by PCR.

In some embodiments, the method of human identification comprises determining the allele of a genetic marker D6S1043 on a first chromosome, wherein the marker comprises a SNP from Table 1; and determining the allele of genetic marker D6S1043 on a second chromosome, wherein the marker does not comprise a SNP from Table 1, wherein the allele of the genetic marker is amplified by an oligonucleotide primer pair, wherein one primer of the primer pair comprises a nucleobase or a universal base complementary to the SNP of SEQ ID NO:5, by a polymerase chain reaction (PCR) and the allele is identified by capillary electrophoresis. In some embodiments, neither primer of the primer pair comprises a nucleobase complementary to the SNP. In some embodiments, the genetic marker of the first chromosome and the genetic marker of the second chromosome are amplified by PCR.

In some embodiments, the method of human identification comprises identifying the allele of genetic marker D13S317 in an individual having a SNP of Table 1 in D13S317, wherein the allele is amplified by an oligonucleotide primer pair, wherein one primer of the primer pair comprises a nucleobase or universal base complementary to the SNP of SEQ ID NO:1, by a polymerase chain reaction (PCR) and the allele is identified by capillary electrophoresis. In some embodiments, neither primer of the primer pair comprises a nucleobase complementary to the SNP. In some embodiments, the genetic marker of the first chromosome and the genetic marker of the second chromosome are amplified by PCR.

In some embodiments, the method of human identification comprises identifying the allele of genetic marker TH01 in an individual having a SNP of Table 1 in TH01, wherein the allele is amplified by an oligonucleotide primer pair, wherein one primer of the primer pair comprises a nucleobase or universal base complementary to the SNP of SEQ ID NO:2, by a polymerase chain reaction (PCR) and the allele is identified by capillary electrophoresis. In some embodiments, neither primer of the primer pair comprises a nucleobase complementary to the SNP. In some embodiments, the genetic marker of the first chromosome and the genetic marker of the second chromosome are amplified by PCR.

In some embodiments, the method of human identification comprises identifying the allele of genetic marker vWA in an individual having at least one of the SNPs of Table 1 in TH01, wherein the allele is amplified by an oligonucleotide primer pair, wherein one primer of the primer pair comprises a nucleobase or universal base complementary to at least one of the SNPs of SEQ ID NO:3, by a polymerase chain reaction (PCR) and the allele is identified by capillary electrophoresis. In some embodiments, neither primer of the primer pair comprises a nucleobase complementary to at least one of the SNPs. In some embodiments, the genetic marker of the first chromosome and the genetic marker of the second chromosome are amplified by PCR.

In some embodiments, the method of human identification comprises identifying the allele of genetic marker D12S391 in an individual having a SNP of Table 1 in D12S391, wherein the allele is amplified by an oligonucleotide primer pair, wherein one primer of the primer pair comprises a nucleobase or universal base complementary to the SNP of SEQ ID NO:4, by a polymerase chain reaction (PCR) and the allele is identified by capillary electrophoresis. In some embodiments, neither primer of the primer pair comprises a nucleobase complementary to the SNP. In some embodiments, the genetic marker of the first chromosome and the genetic marker of the second chromosome are amplified by PCR.

In some embodiments, the method of human identification comprises identifying the allele of genetic marker D6S1043 in an individual having a SNP of Table 1 in D6S1043, wherein the allele is amplified by an oligonucleotide primer pair, wherein one primer of the primer pair comprises a nucleobase or universal base complementary to the SNP of SEQ ID NO:5, by a polymerase chain reaction (PCR) and the allele is identified by capillary electrophoresis. In some embodiments, neither primer of the primer pair comprises a nucleobase complementary to the SNP. In some embodiments, the genetic marker of the first chromosome and the genetic marker of the second chromosome are amplified by PCR.

In other embodiments, included are kits for human identification. In some embodiments, the kit comprises at least one pair of oligonucleotide primers for PCR amplification of at least one locus selected from D13S317, TH01, vWA, D12S391, and D6S1043 wherein one primer of the pair hybridizes to a SNP nucleobase within a primer binding site of the at least one locus. In some embodiments, the kit further comprises an allelic ladder corresponding to the at least one locus selected from D13S317, TH01, vWA, D12S391, and D6S1043, at least one of a protocol, an enzyme, dNTPs, a buffer, a salt or salts, and a control nucleic acid sample. In some embodiments, the SNP nucleobase is within a sequence selected from SEQ ID NO: 1, SEQ ID NO:2, SEQ ID NO:3, SEQ ID NO:4 and SEQ ID NO:5.

BRIEF DESCRIPTION OF THE DRAWINGS

The skilled artisan will understand that the drawings described below are for illustration purposes only. The drawings are not intended to limit the scope of the present teachings in any way.

FIG. 1 illustrates the nucleotide sequence and position of the novel SNPs in each of the five loci from Table 1.

DESCRIPTION OF EXEMPLARY EMBODIMENTS

For the purposes of interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended claims, the singular forms "a," "an," and "the," include plural referents unless expressly and unequivocally limited to one referent. The use of "or" means "and/or" unless stated otherwise. For illustration purposes, but not as a limitation, "X and/or Y" can mean "X" or "Y" or "X and Y". The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of". The term "and/or" means one or all of the listed elements or a combination of any two or more of the listed element.

The section headings used herein are for organizational purposes only and are not to be construed as limiting the described subject matter in any way. All literature cited in this specification, including but not limited to, patents, patent applications, articles, books, and treatises are expressly incorporated by reference in their entirety for any purpose. In the event that any of the incorporated literature contradicts any term defined herein, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The practice of the present invention may employ conventional techniques and descriptions of organic chemistry, polymer technology, molecular biology (including recombinant techniques), cell biology, biochemistry, and immunology, which are within the skill of the art. Such conventional techniques include oligonucleotide synthesis, hybridization, extension reaction, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), PCR Primer: A Laboratory Manual, and Molecular Cloning: A Laboratory Manual (all from Cold Spring Harbor Laboratory Press, 1989), Gait, "Oligonucleotide Synthesis: A Practical Approach" 1984, IRL Press, London, Nelson and Cox (2000), Lehninger, Principles of Biochemistry $3^{rd}$ Ed., W. H. Freeman Pub., New York, N.Y. and Berg et al. (2002) Biochemistry, $5^{th}$ Ed., W. H. Freeman Pub., New York, N.Y. all of which are herein incorporated in their entirety by reference for all purposes.

The term "allele" as used herein refers to a genetic variation associated with a gene or a segment of DNA, i.e., one of two or more alternate forms of a DNA sequence occupying the same locus.

The term "locus" as used herein refers to a specific position on a chromosome or a nucleic acid molecule. Alleles of a locus are located at identical sites on homologous chromosomes.

As used herein, the term "short tandem repeat (STR) loci" refers to regions of the human genome which contains short, repetitive sequence elements of 3 to 7 basepairs in length. The repeats at a given STR marker do not need to be perfect repeats. Examples of STRs, include but are not limited to, a triplet repeat; SEQ ID NO:6 atcatcatcatcaacatcatc, a 4-peat; SEQ ID NO:7 gatagatagatacatagata, and a 5-peat; SEQ ID NO:8 attgcattgcattgc and so on.

The terms "amplicon," "amplification product" and "amplified sequence" are used interchangeably herein and refer to a broad range of techniques for increasing polynucleotide sequences, either linearly or exponentially and can be the product of an amplification reaction. An amplicon can be double-stranded or single-stranded, and can include the separated component strands obtained by denaturing a double-stranded amplification product. In certain embodiments, the amplicon of one amplification cycle can serve as a template in a subsequent amplification cycle. Exemplary amplification techniques include, but are not limited to, PCR or any other method employing a primer extension step. Other nonlimiting examples of amplification include, but are not limited to, ligase detection reaction (LDR) and ligase chain reaction (LCR). Amplification methods can comprise thermal-cycling or can be performed isothermally. In various embodiments, the term "amplification product" and "amplified sequence" includes products from any number of cycles of amplification reactions.

Also herein, the recitations of numerical ranges by endpoints include all numbers subsumed within that range (e.g., 1 to 5 includes 1, 1.5, 2, 2.75, 3, 3.80, 4, 5, etc.).

As used herein, the term "chromosome" broadly refers to autosomes and sex chromosomes. For example, *Homo sapiens* contain 22 autosomes and 2 sex chromosomes, generally, either two X chromosomes or one X and one Y chromosome.

As used herein, the term "comparing" broadly refers to differences between two or more nucleic acid sequences. The similarity or differences can be determined by a variety of methods, including but not limited to: nucleic acid sequencing, alignment of sequencing reads, gel electrophoresis, restriction enzyme digests, single strand conformational polymorphism, and so on.

The terms "detecting" and "detection" are used in a broad sense herein and encompass any technique by which one can determine the presence of or identify a nucleic acid sequence. In some embodiments, detecting comprises quantitating a detectable signal from the nucleic acid, including without limitation, a real-time detection method, such as quantitative PCR ("Q-PCR"). In some embodiments, detecting comprises determining the sequence of a sequencing product or a family of sequencing products generated using an amplification product as the template; in some embodiments, such detecting comprises obtaining the sequence of a family of sequencing products.

As used herein, "DNA" refers to deoxyribonucleic acid in its various forms as understood in the art, such as genomic DNA, cDNA, isolated nucleic acid molecules, vector DNA, and chromosomal DNA. "Nucleic acid" refers to DNA or RNA in any form. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA molecules. Typically, an "isolated" nucleic acid is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, is generally substantially free of other cellular material or culture medium when produced by recombinant techniques, or free of chemical precursors or other chemicals when chemically synthesized.

As used herein, the term "genome" refers to the complete DNA sequence, containing the entire genetic information, of a gamete, an individual, a population, or a species.

As used herein, the term "genomic DNA" refers to the chromosomal DNA sequence of a gene or segment of a gene, including the DNA sequence of noncoding as well as coding regions. Genomic DNA also refers to DNA isolated directly from cells or chromosomes or the cloned copies of all or part of such DNA.

As used herein, the terms "identification" and "identity" are used interchangeably herein and refer to the identification of the individual and/or gender from which a sample or biological sample originated.

As used herein, the term "multiplex" refers to at least two or more amplification reactions occurring simultaneously within a single amplification reaction vessel.

As used herein, the terms "polynucleotide", "oligonucleotide", and "nucleic acid" are used interchangeably herein and refer to single-stranded and double-stranded polymers of nucleotide monomers, including without limitation 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$, and the like. A polynucleotide may be composed entirely of deoxyribonucleotides, entirely of ribonucleotides, or chimeric mixtures thereof and can include nucleotide analogs. The nucleotide monomer units may comprise any nucleotide or nucleotide analog. Polynucleotides typically range in size from a few monomeric units, e.g. 5-40 when they are sometimes referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytosine, "G" denotes deoxyguanosine, "T" denotes thymidine, and "U" denotes deoxyuridine, unless otherwise noted.

As used herein, the terms "target polynucleotide," "nucleic acid target" and "target nucleic acid" are used interchangeably herein and refer to a particular nucleic acid sequence of interest. The "target" can be a polynucleotide sequence that is sought to be amplified and can exist in the presence of other nucleic acid molecules or within a larger nucleic acid molecule. The target polynucleotide can be obtained from any source, and can comprise any number of different compositional components. For example, the target can be nucleic acid (e.g. DNA or RNA). The target can be methylated, non-methylated, or both. Further, it will be appreciated that "target polynucleotide" can refer to the target polynucleotide itself, as well as surrogates thereof, for example amplification products, and native sequences. In some embodiments, the target polynucleotide is a short DNA molecule derived from a degraded source, such as can be found in, for example, but not limited to, forensics samples (see for example Butler, 2001, Forensic DNA Typing: Biology and Technology Behind STR Markers). The target polynucleotides of the present teachings can be derived from any of a number of sources. These sources may include, but are not limited to, whole blood, a tissue biopsy, lymph, bone, bone marrow, tooth, amniotic fluid, hair, skin, semen, anal secretions, vaginal secretions, perspiration, saliva, buccal swabs, various environmental samples (for example, agricultural, water, and soil), research samples generally, purified samples generally, and lysed cells. It will be appreciated that target polynucleotides can be isolated from samples using any of a variety of procedures known in the art, for example the PrepSEQ™ Kits (from Applied Biosystems), Boom et al., and U.S. Pat. No. 5,234, 809, etc. It will be appreciated that target polynucleotides can be cut or sheared prior to analysis, including the use of such procedures as mechanical force, sonication, restriction endonuclease cleavage, or any method known in the art.

As used herein, the term "universal base" in general refers to a base that can bind to two or more different nucleotide bases present in genomic DNA, without any substantial discrimination, for example a base that can combine with two bases is universal. Examples of universal bases include, but are not limited to, Inosine, Xanthosine, 3-nitropyrrole, 4-nitroindole, 5-nitroindole, 6-nitroindole, and so on.

The term "universal base" refers to a base analog that forms "basepairs" with each of the natural DNA or RNA bases with sufficient affinity to provide for the desired level of hybridization affinity in the oligonucleotide primer of interest.

The term "promiscuous (indiscriminative) base" refers to a natural base or a natural base analog that in addition to the perfect complement match base, forms two hydrogen bonds with two or more natural mismatched bases in DNA or RNA with little discrimination between them.

As used herein, the "polymerase chain reaction" or PCR is a an amplification of nucleic acid consisting of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence (Mullis et al., eds, The Polymerase Chain Reaction, BirkHauser, Boston, Mass. (1994)). Each of the above steps may be conducted at a different temperature, preferably using an automated thermocycler (Applied Biosystems LLC, a division of Life Technologies Corporation, Foster City, Calif.). If desired, RNA samples can be converted to DNA/RNA heteroduplexes or to duplex cDNA by methods known to one of skill in the art. The PCR method also includes reverse transcriptase-PCR and other reactions that follow principles of PCR.

As used herein the term "predominant" refers to the wild-type or most frequently occurring base at a particular nucleic acid position for a single nucleotide polymorphism.

The term "primer" refers to a polynucleotide (oligonucleotide) and analogs thereof that are capable of selectively hybridizing to a target nucleic acid or "template", a target region flanking sequence or to a corresponding primer-binding site of an amplification product; and allows the synthesis of a sequence complementary to the corresponding polynucleotide template, flanking sequence or amplification product from the primer's 3' end. Typically a primer can be between about 10 to 100 nucleotides in length and can provide a point of initiation for template-directed synthesis of a polynucleotide complementary to the template, which can take place in the presence of appropriate enzyme(s), cofactors, substrates such as nucleotides (dNTPs) and the like.

As used herein, the term "amplification primer" refers to an oligonucleotide, capable of annealing to an RNA or DNA region adjacent a target sequence, and serving as an initiation primer for DNA synthesis under suitable conditions well known in the art. Typically, a PCR reaction employs a pair of amplification primers including an "upstream" or "forward" primer and a "downstream" or "reverse" primer, which delimit a region of the RNA or DNA to be amplified. A first primer and a second primer may be either a forward or reverse primer and are used interchangeably herein and are not to be limiting.

As used herein, the term "primer-binding site" refers to a region of a polynucleotide sequence, typically a sequence flanking a target region and/or an amplicon that can serve directly, or by virtue of its complement, as the template upon which a primer can anneal for any suitable primer extension reaction known in the art, for example, but not limited to, PCR. It will be appreciated by those of skill in the art that when two primer-binding sites are present on a double-stranded polynucleotide, the orientation of the two primer-binding sites is generally different. For example, one primer of a primer pair is complementary to and can hybridize with the first primer-binding site, while the corresponding primer of the primer pair is designed to hybridize with the complement of the second primer-binding site. Stated another way, in some embodiments the first primer-binding site can be in a sense orientation, and the second primer-binding site can be in an antisense orientation. A primer-binding site of an amplicon may, but need not comprise the same sequence as or at least some of the sequence of the target flanking sequence or its complement.

Those in the art understand that as a target region is amplified by certain amplification means, the complement of the primer-binding site is synthesized in the complementary amplicon or the complementary strand of the amplicon. Thus, it is to be understood that the complement of a primer-binding site is expressly included within the intended meaning of the term primer-binding site, as used herein.

As used herein, the term "unidentified human nucleic acid sample" refers to human nucleic acid found in biological samples according to the present invention including, but not limited to, for example, hair, feces, blood, tissue, urine, saliva, cheek cells, vaginal cells, skin, for example skin cells contained in fingerprints, bone, tooth, buccal sample, amniotic fluid containing placental cells, and amniotic fluid containing fetal cells and semen. It is contemplated that samples may be collected invasively or noninvasively. The sample can be on, in, within, from or found in conjunction with a fiber, fabric, cigarette, chewing gum, adhesive material, soil or inanimate objects. "Sample" as used herein, is used in its broadest sense and refers to a sample suspected of containing a nucleic acid and can comprise a cell, chromosomes isolated from a cell (e.g., a spread of metaphase chromosomes), genomic DNA, RNA, cDNA and the like. The contiguous string of nucleotides, i.e., polynucleotides, comprises an allele which is found in a gene which resides in a position, called a locus, which is within a chromosome.

As used herein, the term "single nucleotide polymorphism" or SNP, refers to a variation from the most frequently occurring base at a particular nucleic acid position.

As used herein, the terms "polymorphism" and "DNA polymorphism" generally refer to the condition in which two or more different nucleotide sequences in a DNA sequence coexist in the same interbreeding population.

The term "selectively hybridize" and variations thereof means that, under appropriate stringency conditions, a given sequence (for example, but not limited to, a primer) anneals with a second sequence comprising a complementary string of nucleotides (for example, but not limited to, a target flanking sequence or a primer-binding site of an amplicon), but does not anneal to undesired sequences, such as non-target nucleic acids or other primers. Typically, as the reaction temperature increases toward the melting temperature of a particular double-stranded sequence, the relative amount of selective hybridization generally increases and mis-priming generally decreases. A statement that one sequence hybridizes or selectively hybridizes with another sequence encompasses embodiments where the entirety of both of the sequences hybridize to one another and embodiments where only a portion of one or both of the sequences hybridizes to the entire other sequence or to a portion of the other sequence.

As used herein, the term "stringency" refers to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together. The art knows well that numerous equivalent conditions can be employed to comprise low stringency conditions.

As used herein the term "variant" refers to the non-predominant or less frequently occurring base at a particular nucleic acid position. The variant is also referred to as a single nucleotide polymorphism at the particular nucleic acid position.

In some embodiments, the present teachings provide seven newly identified single nucleotide polymorphisms (SNPs) in five human loci; D13S317, TH01, D12S391, D6S1043 and vWA (FIG. 1). vWA has three novel SNPs, the other STR markers had only one new SNP each. The SNPs were discovered while conducting concordance STR assay studies with STR kits such as the AmpF/STR® Identifiler® Kit (Applied Biosystems, LLC, Foster City, Calif.) with new primer sequences that differed from commercial offerings. The concordance studies can identify potential allelic dropout due to primer binding site mutations. The unexpected primer binding site mutations (determined to be novel SNPs) were discovered when using new primer sequences for the STR assays and appeared as allelic dropouts.

The new primer sequences hybridized to new primer binding sites that are in different regions of each of the STR alleles being amplified. Further analysis by cloning and sequencing of the loci from individuals with allelic dropout lead to the discovery of the presence of variant nucleobases (Table 1). The cause of allelic dropout was shown to originate from previously unknown SNPs located within the primer binding sites of each of the alleles within the loci of Table 1.

TABLE 1

| Chr. | Locus | Reference Sequence | SNP Pos. | SNP Predominant | SNP Variant | SEQ ID NO |
|---|---|---|---|---|---|---|
| 13 | D13S317 | ref\|NT_024524.14\| | 63702135 | C | T | 1 |
| 11 | TH01 | ref\|NT_009237.18\| | 2132310 | C | A | 2 |
| 12 | vWA | ref\|NT_009759.16\| | 6033144 | C | T | 3 |
|  |  |  | 6033148 | T | C |  |
|  |  |  | 6033156 | C | T |  |
| 12 | D12S391 | ref\|NT_009714.17\| | 5210273 | C | T | 4 |
| 6 | D6S1043 | ref\|NT_007299.13\| | 3056946 | C | T | 5 |

"Allelic dropout" as used herein refers to the failure or significantly reduced amplification of a target nucleic acid. Allelic dropout can result from failure of a primer's 3' terminus to bind to the primer binding site of a target nucleic acid. As a result there is no amplification of the target nucleic acid.

Identifying a human or identification of the human source of a biological sample(s) can be facilitated by determining the STR profile (i.e., the alleles in the sample) for various loci (e.g., CODIS loci), and comparing the results to an STR profile for the same various loci for a known sample or a database of STR profiles for known individuals. The thirteen CODIS loci are TPDX, D3S1358, FGA, D5S818, CSF1PO, D7S820, D8S1179, THO1, vWA, D13S317, D16S539, D18S51, and D21S11, with AMEL for gender determination. Comparing the STR profile of various loci in an unidentified sample with identified STR profiles can identify the human source of the biological sample, identify the human and/or provide investigative leads of possible perpetrators. Efficiency of obtaining the STR profile of an unknown sample can be facilitated by simultaneously analyzing a plurality of loci in a single reaction vessel.

Designing primers and/or primer pairs for the amplification of each individual locus is well known to the skilled artisan and efforts are progressing to multiplex the amplification of numerous loci in a single tube with primers that do not react with other primers and only hybridize to the primer binding site for which they were designed. The hybridization of the primer pair to the target nucleic acid sequence of the sample is contingent upon the primer hybridization (annealing) temperature used in the PCR amplification reaction which impacts primer binding specificity. The terms "annealing" and "hybridizing", including without limitation variations of the root words hybridize and anneal, are used interchangeably and mean the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions may also contribute to duplex stability. Conditions under which primers anneal to complementary or substantially complementary sequences are well known in the art, e.g., as described in Nucleic Acid Hybridization, A Practical Approach, Hames and Higgins, eds., IRL Press, Washington, D.C. (1985) and Wetmur and Davidson, Mol. Biol. 31:349, 1968. In general, whether such annealing takes place is influenced by, among other things, the length of the complementary portion of the primers and their corresponding primer-binding sites in adapter-modified molecules and/or extension products, the pH, the temperature, the presence of mono- and divalent cations, the proportion of G and C nucleotides in the hybridizing region, the viscosity of the medium, and the presence of denaturants. Such variables influence the time required for hybridization. The presence of certain nucleotide analogs or minor groove binders in the complementary portions of the primers and reporter probes can also influence hybridization conditions. Thus, the preferred annealing conditions will depend upon the particular application. Such conditions, however, can be routinely determined by persons of ordinary skill in the art, without undue experimentation. Typically, annealing conditions are selected to allow primers to selectively hybridize with a complementary or substantially complementary sequence in the corresponding adapter-modified molecule and/or extension product, but not hybridize to any significant degree to other sequences in the reaction.

In some embodiments, the primer pair used to amplify at least one of the STR allele regions of the loci listed in Table 1 is composed of polynucleotide primers. The primers may comprise adenosine (A), thymidine (T), guanosine (G), and cytidine (C), as well as uracil (U), nucleoside analogs (for example, but not limited to, inosine, locked nucleic acids (LNA), non-nucleotide linkers, peptide nucleic acids (PNA), universal bases, and phosphoramidites) and nucleosides containing or conjugated to chemical moieties such as radionuclides (e.g., $^{32}$P and $^{35}$S), fluorescent molecules, minor groove binders (MGBs), or any other nucleoside conjugates known in the art.

Generally, oligonucleotide primers can be chemically synthesized. Primer design and selection is a routine procedure in PCR optimization. One of ordinary skill in the art can easily design specific primers to amplify a target locus of interest, or obtain primer sets from the references listed herein.

As an example of primer selection, primers can be selected by the use of any of various software programs available and known in the art for developing amplification and/or multiplex systems. Exemplary programs include, Primer Express® software (Applied Biosystems, Foster City, Calif.) and Primer3 software (Rozen S, Skaletsky H (2000), "Primer3 on the WWW for general users and for biologist programmers," Krawetz S, Misener S (eds) Bioinformatics Methods and Protocols: Methods in Molecular Biology. Humana Press, Totowa, N.J., pp 365-386). In the example of the use of software programs, sequence information from the region of the locus of interest can be imported into the software. The software then uses various algorithms to select primers that best meet the user's specifications.

In other embodiments, included are primers for amplification of one or more STR loci simultaneously in a single amplification reaction in addition to the loci in Table 1. Such systems simultaneously targeting several loci for analysis are called "multiplex" systems. Several such systems containing multiple STR loci and the Amelogenin, non-STR locus, have been described. See, e.g., AMPFℓSTR® SGMPLUS™ PCR AMPLIFICATION KIT USER'S MANUAL, Applied Biosystems, pp. i-x and 1-1 to 1-16 (2001); AMPFℓSTR® IDENTIFILER® PCR AMPLIFICATION KIT USER'S MANUAL, Applied Biosystems, pp. i-x and 1-1 to 1-10 (2001); J W Schumm et al., U.S. Pat. No. 7,008,771. See J. M. Butler, Forensic DNA Typing, Biology, Technology, and Genetics of STR Markers, $2^{nd}$ Edition, Elsevier, Burlington, (2005).

The present teachings provide for a method for amplifying a locus containing an STR with at least one SNP and an amplification protocol to amplify a selected locus having alleles to generate amplified alleles. In other embodiments, included are a method for selection of appropriate loci within a set of loci, and amplification protocols to generate amplified alleles (i.e., amplicons also termed amplified sequences) from multiple co-amplified loci, the resulting amplicons being designed so as to not overlap in size, and/or can be labeled in such a way as to enable one to differentiate between alleles from different loci. In addition, these methods can be used in the selection of multiple STR loci which are compatible for use with a single amplification protocol. In various embodiments of the present teachings a co-amplification of at least one of the loci of Table 1 with at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 60, at least 70, at least 80, at least 90, and at least 100 or more STR loci is envisioned. At least some of the STR loci can have a maximum amplicon size of less than approximately 200 base pairs, less than approximately 250 base pairs, or less than approximately 300 base pairs. Primer design considerations include avoiding significant homology between primers to avoid primer-dimer formation. Further information on loci selection, primer design and multiplex amplification systems and protocols can be found in U.S. patent application Ser. No. 12/261,506, incorporated by reference herein in its entirety.

In some embodiments, the primer can have at the 3' terminus, at one, at two or at three bases from the 3' terminus either the variant nucleobase of the SNP (e.g., a thymidine, T or its compliment, an adenine, A, e.g., D13S317, Table 1) or a universal base. As known to one of skill in the art, a universal base can bind to any nucleobase. Exemplary universal bases for use herein include, but are not limited to, Inosine, Xanthosine, 3-nitropyrrole (Bergstrom et al., Abstr. Pap. Am. Chem. Soc. 206(2):308 (1993); Nichols et al., Nature 369: 492-493; Bergstrom et al., J. Am. Chem. Soc. 117:1201-1209 (1995)), 4-nitroindole (Loakes et al., Nucleic Acids Res., 22:4039-4043 (1994)), 5-nitroindole (Loakes et al. (1994)), 6-nitroindole (Loakes et al. (1994)); nitroimidazole (Bergstrom et al., Nucleic Acids Res. 25:1935-1942 (1997)), 4-nitropyrazole (Bergstrom et al. (1997)), 5-aminoindole (Smith et al., Nucl. Nucl. 17:555-564 (1998)), 4-nitrobenzimidazole (Seela et al., Helv. Chim. Acta 79:488-498 (1996)), 4-aminobenzimidazole (Seela et al., Helv. Chim. Acta 78:833-846 (1995)), phenyl C-ribonucleoside (Millican et al., Nucleic Acids Res. 12:7435-7453 (1984); Matulic-Adamic et al., J. Org. Chem. 61:3909-3911 (1996)), benzimidazole (Loakes et al., Nucl. Nucl. 18:2685-2695 (1999); Papageorgiou et al., Helv. Chim. Acta 70:138-141 (1987)), 5-fluoroindole (Loakes et al. (1999)), indole (Girgis et al., J. Heterocycle Chem. 25:361-366 (1988)); acyclic sugar analogs (Van Aerschot et al., Nucl. Nucl. 14:1053-1056 (1995); Van Aerschot et al., Nucleic Acids Res. 23:4363-4370 (1995); Loakes et al., Nucl. Nucl. 15:1891-1904 (1996)), including derivatives of hypoxanthine, imidazole 4,5-dicarboxamide, 3-nitroimidazole, 5-nitroindazole; aromatic analogs (Guckian et al., J. Am. Chem. Soc. 118:8182-8183 (1996); Guckian et al., J. Am. Chem. Soc. 122:2213-2222 (2000)), including benzene, naphthalene, phenanthrene, pyrene, pyrrole, difluorotoluene; isocarbostyril nucleoside derivatives (Berger et al., Nucleic Acids Res. 28:2911-2914 (2000); Berger et al., Angew. Chem. Int. Ed. Engl., 39:2940-2942 (2000)), including MICS, ICS; hydrogen-bonding analogs, including N8-pyrrolopyridine (Seela et al., Nucleic Acids Res. 28:3224-3232 (2000)); and LNAs such as aryl-.beta.-C-LNA (Babu et al., Nucleosides, Nucleotides & Nucleic Acids 22:1317-1319 (2003); WO 03/020739). The universal base may include those disclosed by Loakes, Nucl. Acids Res., 29: 2437-2447 (2001); and Wu et al, JACS, 22: 7621-7632 (2000), all of which are hereby incorporated by reference herein.

A suitable universal base at or near the 3' terminus of a PCR primer permits primer binding and extension of the primer surrounding the STR alleles from either of the predominant or variant SNP within the locus of interest, thereby amplifying the STR allele within the locus and so generating of the amplification sequence for which the primers are designed, avoiding the occurrence of allelic dropout.

In some embodiments, amplification methods comprise at least one cycle of amplification, for example, but not limited to, the sequential procedures of: hybridizing primers to primer-specific portions of target sequence or amplification products from any number of cycles of an amplification reaction; synthesizing a strand of nucleotides in a template-dependent manner using a polymerase; and denaturing the newly-formed nucleic acid duplex to separate the strands. The cycle may or may not be repeated.

There are many known methods of amplifying nucleic acid sequences including e.g., PCR. See, e.g., PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. Nos. 4,683,202, 4,683,195, 4,800,159 4,965,188 and 5,333,675 each of which is incorporated herein by reference in their entireties for all purposes.

Nucleic acid amplification techniques are traditionally classified according to the temperature requirements of the amplification process. Isothermal amplifications are conducted at a constant temperature, in contrast to amplifications that require cycling between high and low temperatures. Examples of isothermal amplification techniques are: Strand Displacement Amplification (SDA; Walker et al., 1992, Proc. Natl. Acad. Sci. USA 89:392 396; Walker et al., 1992, Nuc. Acids. Res. 20:1691 1696; and EP 0 497 272, all of which are incorporated herein by reference), self-sustained sequence replication (3SR; Guatelli et al., 1990, Proc. Natl. Acad. Sci. USA 87:1874 1878), the Qβ. replicase system (Lizardi et al., 1988, BioTechnology 6:1197 1202), and the techniques disclosed in WO 90/10064 and WO 91/03573.

Examples of amplification techniques that require temperature cycling are: polymerase chain reaction (PCR; Saiki et al., 1985, Science 230:1350 1354), ligase chain reaction (LCR; Wu et al., 1989, Genomics 4:560 569; Barringer et al., 1990, Gene 89:117 122; Barany, 1991, Proc. Natl. Acad. Sci. USA 88:189 193), ligase detection reaction (LDR), LDR-PCR, strand displacement amplification (Walker et al., Nucleic Acids Res, 20, 1691 (1992); Walker et al., Proc. Nat'l Acad. Sci. U.S.A., 89, 392 (1992)), transcription-based amplification (Kwoh et al., Proc. Nat'l Acad. Sci. U.S.A., 86, 1173 (1989)) and restriction amplification (U.S. Pat. No. 5,102,784), self-sustained sequence replication (or "3SR") (Guatelli et al., Proc. Nat'l Acad. Sci. U.S.A., 87, 1874 (1990)), nucleic acid transcription-based amplification system (TAS), the Qβ replicase system (Lizardi et al., Biotechnology, 6, 1197 (1988)) and Rolling Circle Amplification (see Lizardi et al., Nat Genet. 19:225 232 (1998)), hybridization signal amplification (HSAM), nucleic acid sequence-based amplification (NASBA) (Lewis, R., Genetic Engineering News, 12(9), 1 (1992)), the repair chain reaction (RCR) (Lewis, R., Genetic Engineering News, 12(9), 1 (1992)), boomerang DNA amplification (BDA) (Lewis, R., Genetic Engineering News, 12(9), 1 (1992), and branched-DNA methods. Any of the amplification techniques and methods disclosed herein can be used to practice the claimed invention as would be understood by one of ordinary skill in the art.

A variety of nucleic acid polymerases may be used in the methods described herein. For example, the nucleic acid polymerizing enzyme can be a thermostable polymerase or a thermally degradable polymerase. Suitable thermostable polymerases include, but are not limited to, polymerases isolated from *Thermus aquaticus, Thermus thermophilus, Pyrococcus woesei, Pyrococcus furiosus, Thermococcus litoralis*, and *Thermotoga maritima*. Suitable thermodegradable polymerases include, but are not limited to, *E. coli* DNA polymerase I, the Klenow fragment of *E. coli* DNA polymerase I, T4 DNA polymerase, T5 DNA polymerase, T7 DNA polymerase, and others. Examples of other polymerizing enzymes that can be used in the methods described herein include T7, T3, SP6 RNA polymerases and AMV, M-MLV and HIV reverse transcriptases.

Non-limiting examples of commercially available polymerases that can be used in the methods described herein include, but are not limited to, TaqFS®, AmpliTaq CS (Perkin-Elmer), AmpliTaq FS (Perkin-Elmer), Kentaq1 (AB Peptide, St. Louis, Mo.), Taquenase (ScienTech Corp., St. Louis, Mo.), ThermoSequenase (Amersham), Bst polymerase, Vent$_R$(exo$^-$) DNA polymerase, Reader™ Taq DNA polymerase, VENT™ DNA polymerase (New England Biolabs), DEEPVENT™ DNA polymerase (New England Biolabs), PFU-Turbo™ DNA polymerase (Stratagene), Tth DNA polymerase, KlenTaq-1 polymerase, SEQUENASE™ 1.0 DNA polymerase (Amersham Biosciences), and SEQUENASE 2.0 DNA polymerase (United States Biochemicals).

As is understood by one of skill in the art, the Taq polymerase used in PCR often adds an extra (non-templated) nucleotide to the 3'-end of the PCR product as the template strand is copied. This non-template addition is most often adenosine (A) and results in a PCR product that is one base pair longer than the actual target sequence. A final incubation step can optionally be added after the temperature cycling steps in PCR to allow for completion of the addition of the 3' A to those strands that were missed by the Taq polymerase during the thermal cycling steps. Alternatively, the primer sequence may be selected so as to control the amount of non-templated adenylation, e.g., the use of 5' GTTTCTT sequences as taught in Brownstein et al. (BioTechniques, 20, 1004-1010, (1996).

In other embodiments, the identification of a human is based on the amplification of the loci of Table 1 and the CODIS loci by the polymerase chain reaction method (PCR) resulting in the generation of PCR amplicon(s)/amplified sequence(s) and the detection of the amplicon(s). Detection of the amplified sequence can be via any number of methods, including but not limited to for example, Northern blot (Thomas, P. S., "Hybridization of Denatured RNA and Small DNA Fragments Transferred to Nitrocellulose," Proc. Nat'l. Acad.

Sci. USA, 77:5201-05 (1980), which is hereby incorporated by reference in its entirety), Southern blot (Southern, "Detection of Specific Sequences Among DNA Fragments Separated by Gel Electrophoresis," J. Mol. Biol., 98:503-17 (1975), which is incorporated herein by reference in its entirety), PCR, multiplex PCR (Erlich, et. al., "Recent Advances in the Polymerase Chain Reaction", Science 252: 1643-51 (1991), which is incorporated herein by reference in its entirety), in-situ hybridization (Nucleic Acid Hybridization: A Practical Approach, Haimes and Higgins, Eds., Oxford:IRL Press (1988), which is hereby incorporated by reference in its entirety), in-situ PCR (Haase et al., "Amplification and Detection of Lentiviral DNA Inside Cells," Proc. Natl. Acad. Sci. USA, 87(13):4971-5 (1991), which is hereby incorporated by reference in its entirety), or other suitable hybridization assays known in the art. The amplification of the target nucleic acid and detecting may be carried out using well known sequence-specific amplification methods well-known to persons skilled in the art, and detected by methods including, but not limited to, gel electrophoresis, capillary electrophoresis array-capture, direct sequencing, and mass spectrometry.

In some embodiments, the present teachings include cloning and sequencing of the DNA amplified sequence(s). Each amplified sequence can be cloned into an appropriate vector molecule, followed by isolating and sequencing the DNA to permit identification of the SNP(s) within the amplified sequence. Such cloning methods are well known to persons skilled in the art such as in vitro recombinant techniques, and sequencing by methods including, but not limited to, Sanger sequencing, Maxam-Gilbert sequencing, and pyrosequencing (Ronaghi et al. (1996). "Real-time DNA sequencing using detection of pyrophosphate release". *Analytical Biochemistry* 242(1): 84-89), incorporated by reference herein.

Various methods can be used to analyze the products of the amplified alleles either by analyzing the individual amplified sequences or by analyses of a mixture of amplification products obtained from a multiplex reaction including. Such methods include, but are not limited to, for example, detection of fluorescent labeled products, detection of radioisotope labeled products, silver staining of the amplification products, or the use of DNA intercalator dyes such as ethidium bromide (EtBr) and SYBR® Green cyanine dye to visualize double-stranded amplification products. Fluorescent labels suitable for attachment to primers for use in the present teachings are numerous, commercially available, and well-known in the art. With fluorescent analysis, at least one fluorescent labeled primer can be used for the amplification of each locus. Fluorescent detection may be desirable over radioactive methods of labeling and product detection, for example, because fluorescent detection does not require the use of radioactive materials, and thus avoids the regulatory and safety problems that accompany the use of radioactive materials. Fluorescent detection with labeled primers may also be selected over other non-radioactive methods of detection, such as silver staining and DNA intercalators, because fluorescent methods of detection generally reveal fewer amplification artifacts than do silver staining and DNA intercalators. This is due in part to the fact that only the amplified strands of DNA with labels attached thereto are detected in fluorescent detection, whereas both strands of every amplified product are stained and detected using the silver staining and intercalator methods of detection, which result in visualization of many non-specific amplification artifacts.

In some embodiments employed, fluorescent labeling of primers in a multiplex amplification reaction, generally at least two different labels, at least three different labels, at least four different labels, at least five different labels, and at least six or more different labels can be used to label the two, three, four, five or at least six different primers. When a size marker is used to evaluate the products of the multiplex reaction, the primers used to prepare the size marker may be labeled with a different label from the primers that amplify the loci of interest in the reaction. With the advent of automated fluorescent imaging and analysis, faster detection and analysis of multiplex amplification products can be achieved.

In some embodiments of the present teaching, a fluorophore can be used to label at least one primer of the multiplex amplification, e.g. by being covalently bound to the primer, thus creating a fluorescent labeled primer. In some embodiments, primers for different target loci in a multiplex can be labeled with different fluorophores, each fluorophore producing a different colored product depending on the emission wavelength of the fluorophore. These variously labeled primers can be used in the same multiplex reaction, and their respective amplification products subsequently analyzed together. Either the forward or reverse primer of the pair that amplifies a specific locus can be labeled, although the forward can more often be labeled.

The following are some examples of possible fluorophores well known in the art and suitable for use in the present teachings. The list is intended to be exemplary and is by no means exhaustive. Some possible fluorophores include: fluorescein (FL), which absorbs maximally at 492 nm and emits maximally at 520 nm; N,N,N',N'-tetramethyl-6-carboxyrhodamine (TAMRA™ dye), which absorbs maximally at 555 nm and emits maximally at 580 nm; 5-carboxyfluorescein (5-FAM™ dye), which absorbs maximally at 495 nm and emits maximally at 525 nm; 2',7'-dimethoxy-4',5'-dichloro-6-carboxyfluorescein (JOE™ dye), which absorbs maximally at 525 nm and emits maximally at 555 nm); 6-carboxy-X-rhodamine (ROX™ dye), which absorbs maximally at 585 nm and emits maximally at 605 nm; CY3™ dye, which absorbs maximally at 552 nm and emits maximally at 570 nm; CY5™ dye, which absorbs maximally at 643 nm and emits maximally at 667 nm; tetrachloro-fluorescein (TET™ dye), which absorbs maximally at 521 nm and emits maximally at 536 nm; and hexachloro-fluorescein (HEX™ dye), which absorbs maximally at 535 nm and emits maximally at 556 nm; NED™ dye, which absorbs maximally at 546 nm and emits maximally at 575 nm; 6-FAM™ dye, which emits maximally at approximately 520 nm; VIC® dye which emits maximally at approximately 550 nm; PET® dye which emits maximally at approximately 590 nm; LIZ® dye, which emits maximally at approximately 650 nm, and SID™, TED™ and TAZ™ dyes. See SR Coticone et al., U.S. Pat. No. 6,780,588; AMP-FLSTR® IDENTIFILER® PCR AMPLIFICATION KIT USER'S MANUAL, pp. 1-3, Applied Biosystems (2001). Note that the above listed emission and/or absorption wavelengths are only examples and should be used for general guidance purposes only; actual peak wavelengths may vary for different applications and under different conditions.

Various embodiments of the present teachings may comprise a single multiplex system comprising at least four different dyes. These at least four dyes may comprise any four of the above-listed dyes, or any other four dyes capable of producing signals that can be distinguished from one another, e.g., 6-FAM™, VIC®, NED™ and PET® dyes. Other embodiments of the present teaching may comprise a single multiplex system comprising at least five different dyes. These at least five dyes may comprise any five of the above-listed dyes, or any other five dyes capable of producing signals that can be distinguished from one another, e.g., 6-FAM™, VIC®, NED™, PET® and LIZ® dyes. Other embodiments of the present teaching may comprise a single multiplex system comprising at least six different dyes. These at least six dyes may comprise any six of the above-listed dyes, or any other six dyes capable of producing signals that can be distinguished from one another, e.g., 6-FAM™, VIC®, NED™, PET®, LIZ® dyes and a sixth dye (SID™) with maximum emission at approximately 620 nm. In some embodiments, TED dye or TAZ dye can be used in place of SID dye. The various embodiments of the subject method and compositions are not limited to any fixed number of dyes.

The PCR products can be analyzed on a sieving or non-sieving medium. In some embodiments of these teachings, for example, the PCR products can be analyzed by electrophoresis; e.g., capillary electrophoresis, as described in H. Wenz et al. (1998), GENOME RES. 8:69-80 (see also E. Buel et al. (1998), J. FORENSIC SCI. 43:(1), pp. 164-170)), or slab gel electrophoresis, as described in M. Christensen et al. (1999), SCAND. J. CLIN. LAB. INVEST. 59(3): 167-177, or denaturing polyacrylamide gel electrophoresis (see, e.g., J. Sambrook et al. (1989), in MOLECULAR CLONING: A LABORATORY MANUAL, SECOND EDITION, Cold Spring Harbor Laboratory Press, Cold Spring Harbor, N.Y., pp. 13.45-13.57). The separation of DNA fragments in electrophoresis is based primarily on differential fragment size. Amplification products can also be analyzed by chromatography; e.g., by size exclusion chromatography (SEC).

Where fluorescent dyes are used to label amplification products, the electrophoresed and separated products can be analyzed using fluorescence detection equipment such as, for example, the ABI PRISM® 310 or 3130xl genetic analyzer, or an ABI PRISM® 377 DNA Sequencer (Applied Biosystems, Foster City, Calif.); or a Hitachi FMBIO™ II Fluorescent Scanner (Hitachi Software Engineering America, Ltd., South San Francisco, Calif.). In various embodiments of the present teachings, PCR products can be analyzed by a capillary gel electrophoresis protocol in conjunction with such electrophoresis instrumentation as the ABI PRISM® 3130xl genetic analyzer (Applied Biosystems), and allelic analysis of the electrophoresed amplification products can be performed, for example, with GeneMapper® ID Software v3.2, from Applied Biosystems. In other embodiments, the amplification products can be separated by electrophoresis in, for example, about a 4.5%, 29:1 acrylamide:bis acrylamide, 8 M urea gel as prepared for an ABI PRISM®377 Automated Fluorescence DNA Sequencer.

In some embodiments, the detecting step can be combined with an amplifying step, for example, but not limited to, a melt curve determination. Exemplary means for performing a detecting step include the ABI PRISM® Genetic Analyzer instrument series, the ABI PRISM® Sequence Detection Systems instrument series, and the StepOne™ and Applied Biosystems Real-Time PCR instrument series (all from Applied Biosystems); and commercially available microarray and analysis systems available from Affymetrix, Agilent, and Amersham Biosciences, among others (see also Gerry et al., J. Mol. Biol. 292:251-62, 1999; De Bellis et al., Minerva Biotec. 14:247-52, 2002; and Stears et al., Nat. Med. 9:140-45, including supplements, 2003) or bead array platforms (Illumina, San Diego, Calif.). Exemplary software includes GeneMapper™ Software, GeneScan® Analysis Software, Genotyper® Software, and RapidFinder™ Software (all from Applied Biosystems).

In some embodiments the amplified allele is detected by monitoring the increase in the total amount of double-stranded DNA in the reaction mixture as described in Higuchi et al., 1992, BioTechnology 10:413-417; Higuchi et al., 1993, BioTechnology 11:1026-1030; and European Patent Publication Nos. 487,218 and 512,334, each incorporated herein by reference. The detection of double-stranded target DNA relies on the increased fluorescence that ethidium bromide (EtBr) and other DNA binding labels exhibit when bound to double-stranded DNA. The increase of double-stranded DNA resulting from the synthesis of target sequences results in a detectable increase in fluorescence.

The present teachings are also directed to kits for human identification that utilize the methods described above. In some embodiments, a basic kit can comprise a container having at least one pair of oligonucleotide primers for a locus listed in Table 1. A kit can also optionally comprise instructions for use. A kit can also comprise other optional kit components, such as, for example, one or more of an allelic ladder directed to each of the loci amplified, a sufficient quantity of enzyme for amplification, amplification buffer to facilitate the amplification, divalent cation solution to facilitate enzyme activity, dNTPs for strand extension during amplification, loading solution for preparation of the amplified material for electrophoresis, genomic DNA as a template control, a size marker to insure that materials migrate as anticipated in the separation medium, and a protocol and manual to educate the user and limit error in use. The amounts of the various reagents in the kits also can be varied depending upon a number of factors, such as the optimum sensitivity of the process. It is within the scope of these teachings to provide test kits for use in manual applications or test kits for use with automated sample preparation, reaction set-up, detectors or analyzers.

Those in the art understand that the detection techniques employed are generally not limiting. Rather, a wide variety of detection means are within the scope of the disclosed methods and kits, provided that they allow the presence or absence of an amplicon to be determined.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

EXAMPLES

Sample Amplification

The PCR amplification was performed in a reaction volume of 25 μL containing 10 μL of AmpF/STR® NGM™ Master Mix, 5 μL of AmpF/STR® NGM™ Primer Set (Applied Biosystems) and a maximum volume of 104 of target DNA. Samples were amplified in MicroAmp® reaction tubes (Applied Biosystems) in the GeneAmp® PCR System 9700 with a gold-plated silver or silver block (Applied Biosystems). The standard thermal cycling conditions in the 9600 emulation mode consisted of enzyme activation at 95° C. for 11 minutes, followed by 29 cycles of denaturation at 94° C. for 20 sec and annealing and extension at 59° C. for 3 min. A final extension after the temperature cycling steps was performed at 60° C. for 10 min to complete the addition of the 3' A nucleotide. The Taq polymerase used in PCR often adds an extra nucleotide to the 3'-end of the PCR product during primer extension using the DNA sample as the template strand. This non-template addition is most often adenosine and results in a PCR product that is one base pair longer than the actual target sequence. A final incubation step after the temperature cycling steps in PCR completes the addition of the 3' A to those strands that were missed by the Taq polymerase during the thermal cycling steps.

Detection of Amplified Alleles

Amplification products were separated and detected on the Applied Biosystems 3130xl Genetic Analyzer using the specified G5 variable binning module as described in the user guide. For example, sample preparations and electrophoresis on the Applied Biosystems 3130xl analyzer occurred as follows: 1 l of the amplified product or allelic ladder and 0.3 l of GeneScan™-500 LIZ® size standard were added to 8.7 l of deionized Hi-Di™ Formamide (Applied Biosystems), denatured at 95° C. for 3 min, and then chilled on ice for 3 minutes. Samples were injected for 10 s at 3 kV and electrophoresed at 15 kV for 1500 s in Performance Optimized Polymer (POP-4™ polymer) with a run temperature of 60° C. as indicated in the GeneScan36vb_POP4DyeSetG5Module.

This procedure works for the ABI PRISM® 3100, 3100-Avant®, 3130 and 3130xl Genetic Analyzers and assumes previous experience with the ABI PRISM® 3100 or similar capillary electrophoresis instruments. For detailed information about the tasks required to set up the instrument, refer to *ABI PRISM® 3100/3100-Avant Genetic Analyzers Using Data Collection Software v2.0 User Bulletin* (PN 4350218) and *Applied Biosystems 3130/3130xl Genetic Analyzers using Data Collection Software v3.0 User Bulletin* (PN 4363787).

Analysis of Amplified Alleles

Data Analysis Using GeneMapper® IDX Software (GMID)

To import the Next-Generation STR kit panels and bins files into GMID, start GMID, select Tools > "Panel Manager". In the Panel Manager window, select "Panel Manager" in the navigation pane. Select File > "Import Panels," and in the resulting dialog window, navigate to the location where the downloaded Next-Generation panels and bins files were saved. Click to highlight the "Next-Generation_Panels.txt" file and click "Import". "Next-Generation" should now appear in the list of STR kits within the navigation pane. Next, click to highlight the "Next-Generation" entry in the list of kits in the navigation pane. Select File > "Import Bin Set," and in the resulting dialog window, navigate to the location of the downloaded "Next-Generation_Bins.txt" file. Click to select the file and select "Import". Within the larger Panel Manager window, click "OK" to complete importing the panels and bins (this will close the Panel Manager window).

To import the size standard definition file ("GS500LIZ_Next-Generation") into GMID, Select Tools > "GeneMapper Manager". Select the "Size Standards" tab and click "Import". In the dialog window, navigate to the folder to which the downloaded definition file was saved, click to highlight the file and click on the "Import" button. The size standard definition should now appear in the Size Standards drop-down menu in the main GMID samples window. Please note that the Next-Generation Kit size standard definition file has been modified from the standard factory-provided GS500 definition file; the factory-provided version will most likely not work properly for the analysis of Next-Generation STR kit samples.

To import the analysis method file ("Next-Generation_analysis_meth"): Select Tools> "GeneMapper Manager". Select the "Analysis Methods" tab, click the "Import" button, navigate to the location of the downloaded "Next-Generation_analysis_meth" file in the resulting dialog window, and click "Import". The new imported analysis method should then appear in the drop-down Analysis Method menu in the main GMID samples window.

The data were analyzed using GeneMapper® IDX Software as follows: From the project window, select "File > Add samples to project" with the following analysis settings to the samples in the project: a) Analysis method "Next-Generation_Analysis_Meth" b) Panel "Next-Generation" c) Size standard "Y". Allele peaks were interpreted when greater than or equal to 50 relative fluorescence units (RFUs), $3^{rd}$ Order Least Squares size calling method and Full Range for both analysis and sizing.

We claim:

1. A method comprising:
   a. contacting a first primer to a nucleic acid sample to be analyzed;
   b. contacting a second primer to the nucleic acid sample; and
   c. subjecting the nucleic acid sample, the first primer and the second primer to an amplification reaction, and thereby forming an amplification product, wherein the first primer, the second primer or both the first and the second primers are labeled with a non-nucleic acid label, wherein the amplification product comprises SEQ ID NO:1, SEQ ID NO:2, SEQ ID NO:3, SEQ ID NO:4 or SEQ ID NO:5, and wherein SEQ ID NO:1 possesses a thymidine at position 44 from the 5' end, SEQ ID NO:2 possesses an adenosine at position 46 from the 5' end, SEQ ID NO:3 possesses a thymidine at position 3 from the 5' end or a cytosine at position 7 from the 5' end or a thymidine at position 15 from the 5' end, SEQ ID NO:4 possesses a thymidine at position 49 from the 5' end and SEQ ID NO:5 possesses a thymidine at position 33 from the 5' end.

2. The method according to claim 1, wherein the amplification reaction is polymerase chain reaction (PCR).

3. The method according to claim 1, wherein said label is fluorescent.

4. The method according to claim 3, wherein said fluorescent label is selected from 5-carboxyfluorescein, 2'7'-dimethoxy-4'5'-dichloro-6-carboxyfluorescein, fluorescein, N,N,N',N'-tetramethyl-6-carboxyrhodamine, 6-carboxy-X-rhodamine, tetrachloro-fluorescein, and hexachloro-fluorescein.

\* \* \* \* \*

SEQUENCE LISTING

```
<160> NUMBER OF SEQ ID NOS: 8

<210> SEQ ID NO 1
<211> LENGTH: 50
<212> TYPE: DNA
<213> ORGANISM: Homo sapiens

<400> SEQUENCE: 1
ctttagtggg catccgtgac tctctggact ctgacccatc taaygcctat            50

<210> SEQ ID NO 2
<211> LENGTH: 52
<212> TYPE: DNA
<213> ORGANISM: Homo sapiens

<400> SEQUENCE: 2
cctgtacaca gggcttccga gtgcaggtca cagggaacac agactmcatg gt          52

<210> SEQ ID NO 3
<211> LENGTH: 46
<212> TYPE: DNA
```

```
<213> ORGANISM: Homo sapiens

<400> SEQUENCE: 3
tcyatcyatc catcyatcct atgtatttat catctgtcct atctct                    46

<210> SEQ ID NO 4
<211> LENGTH: 52
<212> TYPE: DNA
<213> ORGANISM: Homo sapiens

<400> SEQUENCE: 4
gcactccagg ttctcaggcc ttccacctgg gatggataat tacaccatya gt             52

<210> SEQ ID NO 5
<211> LENGTH: 53
<212> TYPE: DNA
<213> ORGANISM: Homo sapiens

<400> SEQUENCE: 5
tgacttggac tgagatttac acaattggct tcycttgttc tgaggctttt gta            53

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atcatcatca tcaacatcat c                                               21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gatagataga tacatagata                                                 20

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
attgcattgc attgc                                                      15
```